(12) United States Patent
Bak et al.

(10) Patent No.: US 7,851,678 B2
(45) Date of Patent: Dec. 14, 2010

(54) *GUZMANIA* HYBRID NAMED 'RITMO'

(75) Inventors: Elly Bak, Rijsenhout (NL); Nicolaas D. M. Steur, Oude Niedorp (NL)

(73) Assignee: Corn.Bak B.V., Assendelft (NL)

( * ) Notice: Subject to any disclaimer, the term of this patent is extended or adjusted under 35 U.S.C. 154(b) by 295 days.

(21) Appl. No.: 11/979,152

(22) Filed: Oct. 31, 2007

(65) Prior Publication Data
US 2009/0113567 A1 Apr. 30, 2009

(51) Int. Cl.
*A01H 5/00* (2006.01)
*A01H 1/00* (2006.01)
*A01H 1/02* (2006.01)

(52) U.S. Cl. .......... 800/298; 800/260; 800/323
(58) Field of Classification Search ............. 800/298, 800/260, 323; Plt./371
See application file for complete search history.

*Primary Examiner*—Annette H Para
(74) *Attorney, Agent, or Firm*—Foley & Lardner LLP

(57) ABSTRACT

A new and distinct *Guzmania* hybrid named 'RITMO' characterized by solid growth habit; funnel-form rosette plant, measuring about 20 cm in height (above the pot when flowering); numerous, relatively narrow, green color foliage, measuring about 25 cm in length and about 2.4 cm to 2.7 cm in width; superior floral bract production; bracts have a unique orange color which distinguishes this cultivar from typical *Guzmania*; round, spike-like inflorescence, measuring about 5 cm in height and about 11 cm in diameter; and long-lasting habit.

5 Claims, 2 Drawing Sheets
(2 of 2 Drawing Sheet(s) Filed in Color)

GUZMANIA HYBRID NAMED 'RITMO'

FIELD OF THE INVENTION

The present invention relates to a new, distinct and stable hybrid of *Guzmania* hybrid, hereinafter referred to as 'RITMO'. The present invention relates to seeds which are the *Guzmania* hybrid 'RITMO', as well as, plants and plant parts produced by these seeds which have all of the morphological and physiological characteristics of the *Guzmania* hybrid 'RITMO'. The present invention also relates to methods for producing these seeds and plants of the *Guzmania* hybrid 'RITMO'. Furthermore, the present invention relates to a method of producing progeny *Guzmania* plants by crossing *Guzmania* 'RITMO', as either the female or seed or male or pollen parent, with another *Guzmania* plant and selecting progeny.

BACKGROUND OF THE INVENTION

The present invention relates to a new, distinct and stable hybrid of *Guzmania* hybrid, botanically known as *Guzmania lingulata* minor, and hereinafter referred to by the variety denomination 'RITMO'. The new *Guzmania* 'RITMO' originated from a cross made in a controlled breeding program by the inventors in 1998, and then first flowered in 2000, in Assendelft, The Netherlands. The female or seed parent is the *Guzmania lingulata* minor inbred line identified by code 85072 (unpatented). The male or pollen parent is the *Guzmania lingulata* minor inbred line identified by code 9814911 (unpatented).

*Guzmania* is a member of the Bromeliaceae family. *Guzmania* is predominantly epiphytic with a few terrestrial species and is native to the tropics. For the most part, species vary in diameter from 7 or 8 inches to 3 or 4 feet and have rosettes of glossy, smooth-edged leaves.

Floral bracts of *Guzmania* frequently have brilliant colors and may last for many months. The range of colors for *Guzmania* is generally from yellow through orange but may also include flame red and red-purple. White or yellow, tubular, three-petalled flowers may also appear on a stem or within the leaf rosette but are usually short-lived.

*Guzmania* may be advantageously grown as pot plants for greenhouse or home use. Typically, the plants are shaded from direct sunlight. During the spring to autumn period, the central vase-like part of the leaf rosette is normally filled with water.

*Guzmania* is native to tropical America. Leaves of *Guzmania* are usually formed as basal rosettes which are stiff and entire and in several vertical ranks. *Guzmania* plants have terminal spikes or panicles which are often bracted with petals united in a tube about as long as the calyx. The ovary is superior and the seeds plumose.

Asexual propagation of *Guzmania* is frequently performed by vegetative means through the use of tissue culture practices. Propagation of *Guzmania* can also be from offshoots which can be detached from the mother plant and grown in an appropriate soil or bark mixture.

Methods for cultivation and crossing of *Guzmania* are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN, Verlag, Paul Parey, Berlin (1986); and Rauh, Werner, BROMELIEN, Verlag Eugen Ulmer, Stuttgart (1981).

A *Guzmania* inbred is produced by brother/sister crossing over several generations to produce a genetically homozygous plant selection. A hybrid cultivar is produced by crossing two genetically distinct inbred lines, collecting seeds produced by the cross, and germinating seeds so-produced to make hybrid plants. The hybrid seeds and plants produced by this method are uniform with respect their morphological and physiological characteristics.

A need exists for a greater variety of *Guzmania* cultivars with attractive ornamental features. Additionally, a need exists for additional *Guzmania* hybrid cultivars that can be easily propagated by seed. The new *Guzmania* 'RITMO' was developed through a controlled breeding program and exhibits unique, desirable and stable characteristics.

SUMMARY OF THE INVENTION

The present invention provides *Guzmania* plant selections that are solid, small-sized, long-lasting hybrids with superior bract production and an orange inflorescence that exhibits good keeping quality. The present invention also provides *Guzmania* plant selections with a round, spike-like inflorescence with a unique orange color which distinguishes the new cultivar from typical *Guzmania*.

These and other objectives have been achieved in accordance with the present invention which provides 'RITMO' as a new *Guzmania* cultivar that is a product of a planned breeding program conducted by the inventors, Elly Bak and Nico D. M. Steur, in Assendelft, The Netherlands, in 1998. The female or seed parent is the *Guzmania lingulata* minor inbred line identified by the code 85072 (unpatented). The male or pollen parent is the *Guzmania lingulata* minor inbred line identified by the code 9814911 (unpatented).

Both parental cultivars have a sufficient degree of homozygosity such that the progeny of the cross are genetypically and phenotypically uniform. The cultivar 'RITMO' therefore can be produced by sexual reproduction by crossing the parental inbred lines identified by the codes 85072 and 9814911 to produce a population of progeny plants, each of which has the combination of characteristics as herein disclosed for the new cultivar 'RITMO'.

Seeds which are cultivar 'RITMO' are produced by crossing the parental inbred lines identified by the codes 85072 and 9814911, and are deposited with the American Type Culture Collection, 10801 University Boulevard, Manassas, Va. 20110-2209 (ATCC Patent Deposit Designation No. PTA-8635). 2500 seeds were deposited with the ATCC on Sep. 19, 2007.

OBJECTS OF THE INVENTION

The present invention relates to seeds which produce *Guzmania* cultivar 'RITMO'. The present invention also relates to *Guzmania* plants, and parts thereof, having all the physiological and morphological characteristics of *Guzmania* cultivar 'RITMO'. The present invention relates to a plant produced from seeds which are *Guzmania* cultivar 'RITMO'. The present invention also relates to plant parts, such as pollen, seeds or inflorescence produced by *Guzmania* cultivar 'RITMO'.

The present invention relates to method of producing seed which are *Guzmania* cultivar 'RITMO', by crossing *Guzmania lingulata* minor inbred line identified by code 85072 (unpatented) as the female or seed parent with *Guzmania lingulata* minor inbred line identified by code 9814911 (unpatented) as the male or pollen parent, and the reciprocate cross with 9814911 as the male parent and 85072 as the female parent, and harvesting seeds produced from said crosses.

The present invention also relates to a method of producing plants having all the physiological and morphological characteristics of the *Guzmania* cultivar 'RITMO' comprising the steps of (a) crossing *Guzmania lingulata* minor inbred line identified by code 85072 (unpatented) as the female or seed parent with *Guzmania lingulata* minor inbred line identified by code 9814911 (unpatented) as the male or pollen parent; (b) harvesting seeds produced from said cross; and (c) producing plants from said harvested seeds.

The present invention also relates to producing progeny plants from the cross of *Guzmania* cultivar 'RITMO', as the female or male parent, with another *Guzmania* plant, and selecting progeny plants from this cross.

BRIEF DESCRIPTION OF THE PHOTOGRAPHS

The patent or application file contains at least one drawing executed in color. Copies of this patent or patent application publication with color drawings will be provided by the Office upon request and payment of the necessary fees.

The accompanying photographs illustrate the overall appearance of the new *Guzmania* cultivar 'RITMO' showing the color s as true as is reasonably possible with colored reproductions of this type. Colors in the photographs may differ slightly from the color values cited in the detailed botanical description which accurately describes the color of 'RITMO'.

DETAILED BOTANICAL DESCRIPTION

Figure 1:
FIG. 1 shows a side view perspective of the primary and top bracts produced by a typical potted, flowering plant of 'RITMO', at 17 months of age.
Figure 2:
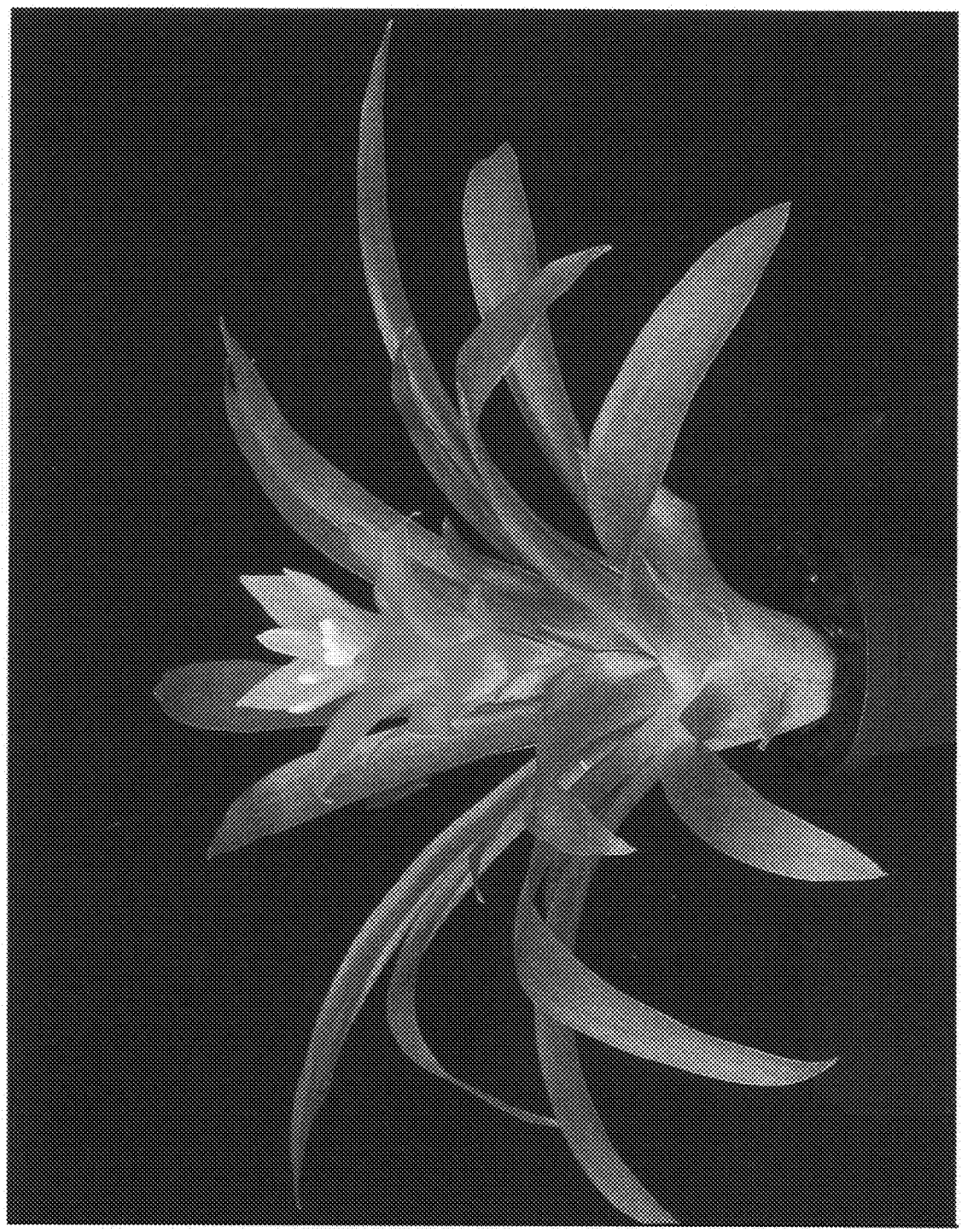
FIG. 2 shows a close-up top view perspective of the inflorescence and top bracts produced by a typical potted, flowering plant of 'RITMO', at 17 months of age.

The present invention was created by the inventors, Elly Bak and Nicolaas D. M. Steur in 1998, and flowered for the first time in 2000 in Assendeltt, The Netherlands.

This invention is directed to *Guzmania* plant having all the morphological and physiological characteristics of the cultivar 'RITMO' produced from seeds which are the product of the cross of the *Guzmania lingulata* minor inbred line identified by code 85072 (unpatented) as the female or seed parent with the *Guzmania lingulata* minor inbred line identified by code 9814911 (unpatented) as the male or pollen parent. Both parents have a sufficient degree of homozygosity such that the progeny of the cross were, and continue to be, phenotypically uniform. The new cultivar 'RITMO' can therefore be produced by sexual reproduction by crossing of the inbred selections identified by the codes 85072 and 9814911 to produce a population of progeny plants, each of which has the combination of characteristics herein disclosed for the new cultivar 'RITMO'.

The new cultivar 'RITMO' can also be produced by asexually reproducing progeny from the cross of the *Guzmania lingulata* minor inbred lines identified by the codes 85072 and 9814911. Asexual reproduction of the new cultivar by vegetative means by cuttings was first performed in 2002, in Assendelft, The Netherlands. The first 'RITMO' plants propagated through the use of cuttings flowered in 2003, in Assendelft, The Netherlands, and have demonstrated that the new cultivar reproduces true-to-type and that the combination of characteristics as herein disclosed for the new cultivar are firmly fixed and retained through successive generations of asexual reproduction. Sexual propagation has demonstrated that the combination of characteristics as herein disclosed for the new cultivar 'RITMO', as observed in Assendelft, The Netherlands, are firmly fixed and are retained through successive generations of asexual reproduction.

BRIEF DESCRIPTION OF THE INVENTION

The following traits have been repeatedly observed and are determined to be unique characteristics of 'RITMO' which in combination distinguish this *Guzmania* as a new and distinct cultivar:
1. Solid growth habit;
2. Funnel-form rosette plant, measuring about 20 cm in height (above the pot when flowering);
3. Numerous, relatively narrow, green color foliage, measuring about 25 cm in length and about 2.4 cm to 2.7 cm in width;
4. Superior floral bract production;
5. Bracts have a unique orange color which distinguishes this cultivar from typical *Guzmania*;
6. Round, spike-like inflorescence, measuring about 5 cm in height and about 11 cm in diameter; and
7. Long-lasting habit.

Of the many commercial cultivars known to the present inventors, the most similar in comparison to the new *Guzmania* cultivar 'RITMO' is the *Guzmania* cultivar 'TEMPO' (granted, U.S. Pat. No. 6,403,868). Plants of the new cultivar 'RITMO' differ from plants of 'TEMPO' primarily in inflorescence color. Plants of 'RITMO' produce inflorescence which are orange in color whereas plants of 'TEMPO' produce inflorescence which are red in color.

'RITMO' has not be entested and observed under all possible environmental conditions. The phenotype of the new cultivar may vary with variations in environment such as temperature, light intensity, frequency of fertilization, composition of fertilizer, acetylene treatment, day length and humidity, without any change in the genotype of the plant.

For example, substantial differences in plant height and diameter, number of leaves, can result depending on the size of the plant at the time that flowering is induced by acetylene treatment. Since treatment with acetylene to induce flowering disrupts normal watering and fertilization regimens, acetylene treatment of relatively smaller plants adversely affects the growth of the plant.

The aforementioned photographs, together with the following observations, measurements and values describe the new *Guzmania* 'RITMO' as grown in a greenhouse in Assendelft, The Netherlands, under conditions which closely approximate those generally used in commercial practice. Plants of 'RITMO' were grown in a greenhouse with day temperatures ranging from 20° C. to 28° C. and night temperatures ranging from 18° C. to 23° C. No artificial lighting or photoperiodic treatments were conducted, but plants of 'RITMO' are forced into flowering by adding acetylene. The following fertilizer is added when growing plants of 'RITMO': 1 part nitrogen, 0.6 parts phosphor, 2 parts Kalium and 0.1 parts magnesium.

Color references are made to the Royal Horticultural Society Colour Chart (RHS), except where general colors of ordinary significance are used. Color values were taken under daylight conditions in a greenhouse in Assendelft, The Netherlands. The age of the plants of 'RITMO' described is about 10 weeks after treatment with acetylene.

Classification:
Botanical: *Guzmania* sp.

Parentage:
Female Parent: *Guzmania lingulata* minor inbred line identified by code 85072 (unpatented)
Male Parent: *Guzmania lingulata* minor inbred line identified by code 9814911 (unpatented)

Plant:
  General Appearance and Form:
    Height: About 18 cm to 20 cm (when flowering)
    Width: About 30 cm to 40 cm
    Shape: Funnel form rosette
  Growth habit: Stemless
  Plant Vigor: Good
  Flowering Season: A fully grown plant can flower year round, starting 10 to 12 weeks after induction of natural light or trough treatment with acetylene.
  Cold Tolerance: Frost tender. Temperatures below 5° C. may damage plants.
  Fragrance: None Foliage:
  Quantity: About 25 (depending on the size of the plant)
  Size of Leaf:
    Length: About 20 cm to 25 cm
    Width: About 2.4 cm to 2.7 cm
  Overall Shape: Linear
  Apex Shape: Acute
  Base Shape: Strap-like around central axis
  Margin: Entire
  Texture: Smooth
  Color: Leaf color can vary somewhat depending on growing conditions
    Upper Surface:
      Mature leaf: Green, RHS 137B
      Immature leaf: Green, RHS 137B
    Lower Surface:
      Mature leaf: Green, RHS 137C
      Immature leaf: Green, RHS 137C
  Venation: None Inflorescence:
Borne: Erect stalks
Shape: Round, spike-like head
Size:
  Length: About 5 cm
  Diameter: About 11 cm
  Time of Bloom: A fully grown plant can produce an inflorescence containing about 20 flowers (depending on the size of the plant), and can bloom the whole year starting about ten (10) to twelve (12) weeks after natural induction or through treatment with acetylene.
  Duration of Bloom: Each flower blooms one (1) day and the total blooming of the whole inflorescence is about five (5) weeks.
Petals:
  Number: 3 per flower
  Length: About 6.0 cm
  Width: About 0.6 cm
  Apex Shape: Obtuse
  Base Shape: Fused
  Color: Primarily RHS 17C, yellow orange, and RHS155D, white, at the apex.
Sepals:
  Number: 3 per flower
  Length: About 2 cm
  Width: About 0.2 cm
  Apex Shape: Acute
  Base Shape: Fused
  Color: RHS 155A, white.

Bracts:
Scape Bracts:
  Quantity: About 6
  Arrangement: Alternate
  Size:
    Length: About 12 cm (lowest) to about 9 cm (scape bracts positioned just below the primary bracts).
    Width: About 3.5 cm
  Overall shape: Lanceolate
  Apex shape: Acute
  Base shape: Fused
  Margin: Entire
  Texture: Smooth
  Color:
    Upper surface: RHS 137B, green
    Under surface: RHS 137C, green
Primary Bracts:
  Quantity: About 10
  Arrangement: Alternate
  Size:
    Length: About 7.5 cm (lowest) to about 5 cm (primary bracts become shorter closer to the top of plant)
    Width: About 2.5 cm
  Overall shape: Lanceolate
  Apex shape: Acute
  Base shape: Fused
  Margin: Entire
  Texture: Smooth
  Color:
    Upper surface: RHS 30A, orange-red.
    Under surface: RHS 30A, orange-red.
    Tip of top primary bracts: RHS 23A, yellow-orange.
Floral bracts: Disposed within the inflorescence.

Reproductive Organs:
Androecium:
  Stamen:
    Number: 6 per flower
    Length: About 5.5 cm
    Diameter: Less than 1 mm
    Color: White
  Anther:
    Length: About 0.5 cm
    Color: White
  Pollen:
    Amount: Scarce
    Color: White
Gynoecium:
  Pistil:
    Number: 1 per flower
    Length: About 5 cm
  Stigma:
    Shape: 3-parted
    Width: About 1 mm
    Color: White
  Style:
    Length: About 5 cm
    Color: White
  Ovary:
    Position: Superior
    Shape: Conical
    Length: About 1 cm
    Diameter: About 0.5 cm
    Color: Light green Seeds:
- Quantity: About 4000 seeds, divided among about 20 capsules (depending on the size of the plant). Since the new cultivar is a hybrid, the seeds produced by the plant can not be used for reproduction.
- Size:
  - Length: About 4 mm
  - Diameter: Less than 1 mm
- Texture: Plumose
- Color: Brown Fruit:
- Quantity: About 20 (depending on size of plant)
- Type: Capsule
- Size:
  - Length: About 3.0 cm
  - Diameter: About 0.6 cm Disease/Pest Resistance: No observations made.

Disease/Pest Susceptibility: No observations made.

We claim:

1. A *Guzmania* plant named 'RITMO', obtained from seed having American Type Culture Collection (ATCC) Patent Deposit Designation No.: PTA-8635.

2. *Guzmania* seed having American Type Culture Collection (ATCC) Patent Deposit Designation No.: PTA-8635.

3. Plants parts obtained from the *Guzmania* plant of claim 1.

4. A method of producing *Guzmania* progeny plant, method which comprises the steps of (a) crossing *Guzmania* 'RITMO' produced from seed accorded American Type Culture Collection (ATCC) Patent Deposit Designation No.: PTA-8635 as a female or male parent with another *Guzmania* plant, and (b) selecting progeny.

5. The method according to claim 4, wherein the second *Guzmania* plant is 'RITMO'.

* * * * *